United States Patent [19]
Anelli et al.

[11] Patent Number: 5,464,607
[45] Date of Patent: Nov. 7, 1995

[54] 5,5'-/(1,3-PROPANEDIYL) BIS-/IMINO(2-OXO-2,1-ETHANEDIYL) ACETYLIMINO/BIS(2,4,6-TRIIODO-1,3-BENZENEDICARBOXYLAMIDES), AND CONTRAST MEDIA CONTAINING THEM

[75] Inventors: Pierlucio Anelli; Marino Brocchetta; Fulvio Uggeri; Massimo Visigalli, all of Milan, Italy

[73] Assignee: Dibra S.p.A., Milan, Italy

[21] Appl. No.: 244,598

[22] PCT Filed: Dec. 1, 1992

[86] PCT No.: PCT/EP92/02770

§ 371 Date: Jun. 1, 1994

§ 102(e) Date: Jun. 1, 1994

[87] PCT Pub. No.: WO93/12071

PCT Pub. Date: Jun. 24, 1993

[30] Foreign Application Priority Data

Dec. 10, 1991 [IT] Italy .................. MI91A3305

[51] Int. Cl.$^6$ .................................. C07C 235/68
[52] U.S. Cl. ........................... 424/9.452; 564/153
[58] Field of Search ..................... 564/153; 424/5

[56] References Cited

U.S. PATENT DOCUMENTS

| | | | |
|---|---|---|---|
| 3,632,738 | 1/1972 | Ingelman et al. | 424/5 |
| 4,014,986 | 3/1977 | Tilly et al. | 424/5 |
| 4,239,747 | 12/1980 | Pfeiffer et al. | 454/5 |
| 4,264,572 | 4/1981 | Klieger et al. | 424/5 |
| 4,348,377 | 9/1982 | Felder et al. | 424/5 |
| 4,367,216 | 1/1983 | Mutzel et al. | 424/5 |
| 5,004,835 | 4/1991 | Blaszkiewicz et al. | 424/5 |
| 5,349,085 | 9/1994 | Hansen et al. | 424/5 |

FOREIGN PATENT DOCUMENTS

| | | | |
|---|---|---|---|
| 108638 | 5/1984 | European Pat. Off. | 424/5 |
| 317492 | 5/1989 | European Pat. Off. | 424/5 |

*Primary Examiner*—Glennon H. Hollrah
*Assistant Examiner*—Scott C. Rand
*Attorney, Agent, or Firm*—Bucknam and Archer

[57] ABSTRACT

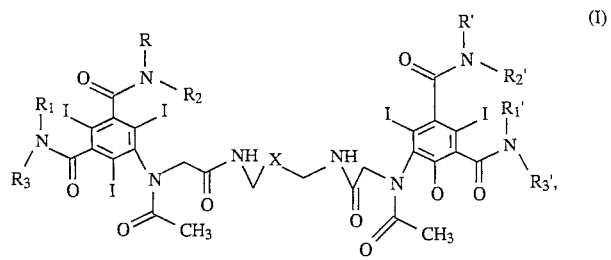

(I)

wherein R, R', $R_1$, and $R_1$', which are the same or different, are H, $C_1$–$C_4$ alkyl, linear or branched $C_1$–$C_4$ mono- or polyhydroxyalkyl;

$R_2$, $R_2$', $R_3$, and $R_3$', which are the same or different, are one of the groups of formula —$CH_2CH_2OH$, —$CH_2CH(OH)CH_2OH$ —$CH(CH_2OH)CH(OH)CH_2OH$, —$CH_2(CHOH)_4CH_2OH$, or —$CH(CH_2OH)_2$; and X is one of the groups —$CH(OH)$—, —$CH(CH_2OH)$—, —$C(OH)(CH_2OH)$—, or —$C(CH_2OH)_2$—, are useful as opacifying components for X-ray contrast media.

8 Claims, No Drawings

5,5'-/(1,3-PROPANEDIYL) BIS-/IMINO(2-OXO-2,1-ETHANEDIYL) ACETYLIMINO/BIS(2,4,6-TRIIODO-1,3-BENZENEDICARBOXYLAMIDES), AND CONTRAST MEDIA CONTAINING THEM

This application is a 371 of PCT/EP92/02770, filed Dec. 1, 1992.

This invention relates to symmetrical and asymmetrical 5,5'-[(1,3-propanediyl)bis[imino(2-oxo-2,1-ethanediyl) acetylimino]]bis(2,4,6-triiodo-1,3-benzenedicarboxyamides), useful as opacifyng component of X-ray contrast media, of general formula (I)

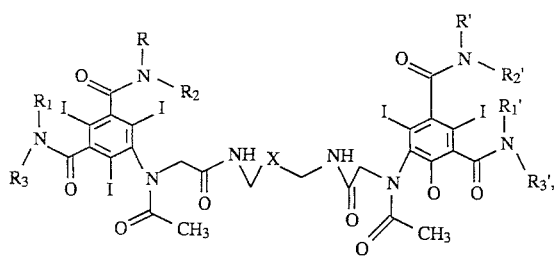

wherein:

$R, R', R_1, R_1'$, which are the same or different, are H, $C_1$–$C_4$ alkyl, linear or branched $C_1$–$C_4$ mono- or polyhydroxyalkyl, $R_2, R_2', R_3, R_3'$, which are the same or different, are one of the groups of formula —$CH_2CH_2OH$, —$CH_2CH(OH)CH_2OH$, —$CH(CH_2OH)CH(OH)CH_2OH$, —$CH_2(CHOH)_4CH_2OH$ or —$CH(CH_2OH)_2$, X is one of the groups —CH(OH)—, —CH($CH_2OH$)—, —C(OH)($CH_2OH$)— or —C($CH_2OH$)$_2$—, as well as enantiomers, diastereoisomers and/or rotamers thereof.

This inventions also includes the process for preparing these non-ionic compounds, as well as the X-ray contrast media containing them as opacifying components.

Preferred compounds of formula (I) are those in which R, R', $R_1$, $R_1'$ are H or $CH_3$ and X is —CH(OH)— or —C($CH_2OH$)$_2$—. Particularly preferred are those in which R, R', $R_1$, $R_1'$ are H and X is —CH (OH)—.

Compounds of formula (I) belong to the class of non-ionic contrast media for X-ray diagnosis, which are more and more replacing the salts of 2,4,6-triiodo-benzoic acid derivatives, up to now widely used, in view of their better tolerabi lity and minimum tendency to produce side effects. Thanks to the elimination of ionic species, non-ionic solutions, in comparison with ionic agents, are characterized by the same iodine content and a lower osmotic pressure, therefore a lower osmolality. For this reason, for instance in angiography, they cause less pain and lower endothelial damages. And in subarachnoidal administration used in myelography or cysternography, cases of arachnoiditis or epileptical episodes are very rare while they are frequent when ionic contrast media are used. Unfortunately, despite their remarkable physical and pharmacological properties, non-ionic contrast media, basically Consisting of monocyclic aromatic triiodinated nuclei, are too much hypertonic at the high dosages and concentrations required for many specific examinations. This fact led to the development of hexaiodinated dimeric products, in which osmolality is further reduced in accordance with iodine concentration. However, the concentrated solutions of those compounds are often too much viscous. In addition, a large number of products, although theoretically promising, are not enough soluble.

For this reason, research efforts have been paid on new hexaiodinated dimeric products characterized by high solu bility, low viscosity and osmolality as well as i.v., intracisternal and intracerebral high tolerability and minimum side effects (pain, temperature raise, nausea, pressure lowering and vessel damages).

In particular physicians need new contrast media covering many different uses, for instance urography, angiography, cardioangiography, phlebography, myelography, cysternography, lymphography, istersalpingography, bronchography and gastrography as well as articular cavities visualization.

The compounds of the present invention are generally characterized by a good water solubility, in some cases exceeding 100 g of compound per 100 ml of solution at 30° C.

Furthermore their solutions are low osmolar but surprisingly without bringing about the expected increase in viscosity.

For instance, one of the preferred compounds of this invention, 5,5'-[(2-hydroxy-1,3-propanediyl) bis-[imino(2-oxo-2,1-ethanediyl)acetylimino]] bis-[$\underline{N}$, $\underline{N}$'-bis-(2,3-dihydroxypropyl)-2,4,6-triiodo-1,3- benzenedicarboxyamide], produces stable aqueous solutions at 30° C. containing more than 100 g of product per 100 ml of solution, as indicated in Table 1 which also includes the good values of osmolality and viscosity obtained for said compound.

TABLE 1

| Chemico-physical characteristics of the compound of formula (I): 5,5'-[(2-hydroxy-1,3-propanediyl)bis[imino(2-oxo-2,1-ethanediyl)-acetylimino]]bis[N,N'-bis(2,3-dihydroxypropyl)-2,4,6-triiodo-1,3-benzenedicarboxyamide] Solubility in H₂O at 30° C.: > 100 g in 100 ml | | | |
|---|---|---|---|
| Iodine concentration | 200 mgI/ml | 300 mgI/ml | 400 mgI/ml |
| | Osmolality[a)] | | |
| Osmolality (osmol/kg H₂O) | 0,17 | 0,25 | 0,72 |
| | Viscosity at 20° C.[b)] | | |
| Viscosity (mPa · s) | 5,7 | 24 | 112 |
| | Viscosity at 37° C.[b)] | | |
| Viscosity (mPa · s) | 3,4 | 12 | 41 |

[a)]Calculated with a steam-pressure osmometer Wescor(R) mod 5500, calibrated with NaCl aqueous solutions.
[b)]Calculated with ROTOVISCO(R)RV100-CV100-LV100, sensor ZB15.

The process for the preparation of 5,5'-[(2-hydroxy-1,3-propanediyl) bis[imino(2-oxo-2,1-ethanediyl) -acetylimino]] bis(2,4,6-triiodo-1,3-benzenedicarboxyamides) of formula (I) is characterised in that a $\underline{N}$, $\underline{N}$'-1,3-propanediyl-bis(2-chloroacetamide) of formula (II)

$$ClCH_2OC—NH—CH_2—X—CH_2—NH—COCH_2Cl \quad (II),$$

where X is one of the groups —CH(OH)—, —CH($CH_2OH$)—, —C(OH)($CH_2OH$)— or —C($CH_2OH$)$_2$—, in which hydroxy groups have been protected by an adequate protective group, is reacted, directly or through a multistep process, with a 5-acetylamino-2,4,6-triiodo-isophthaldiamide reactive derivative of general formula (III)

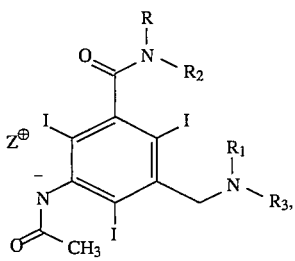

wherein:

R and $R_1$ which are the same or different, are H, $C_1$–$C_4$ alkyl, linear or branched $C_1$–$C_4$ mono- or polyhydroxyalkyl, $R_2$ and $R_3$, which are the same or different, are one of the groups of formula —$CH_2CH_2OH$, —$CH_2CH(OH)CH_2OH$, —$CH(CH_2OH)CH(OH)CH_2OH$, —$CH_2(CHOH)_4CH_2OH$ or —$CH(CH_2OH)_2$, Z is an alkali metal ion, preferably $Na^+$ or $K^+$, and, after deprotecting the hydroxy groups, the corresponding compound of general formula (I) is obtained, according to one of the two preferred procedures:

a) a compound of formula (II) is reacted in a solvent with a compound of formula (III) in a molar ratio ranging from 1:2 to 1:2.5, thereafter the remaining protective groups are hydrolysed in an acid medium in order to directly obtain the corresponding compound of formula (I), b) a compound of formula (II) is reacted in a solvent with a compound of formula (III) in a molar ratio ranging from 1:1 to 1:0.5 to give the compound of formula (IV)

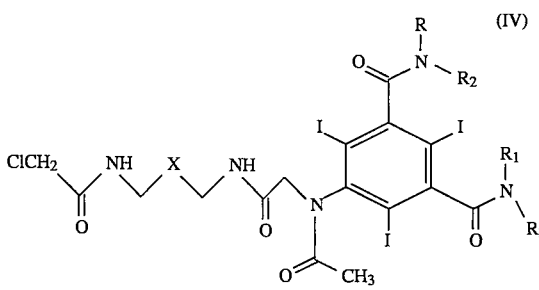

wherein R, $R_1$, $R_2$, $R_3$, X are as previously described, and said compound (IV) is then reacted in a solvent with another compound of formula (III) in a molar ratio ranging from 1:1 to 1:1.2, thereafter the remaining protective groups are hydrolysed in an acid medium to give the corresponding compound of formula (I).

If a direct reaction of the compound of formula (II) with a compound of formula (III) is performed according to synthesis a), symmetrical products with two identical aromatic iodinated residues are obtained.

If a multistep reaction is performed according to synthesis b), asymmetrical products with two different iodinated aromatic residues are obtained.

The reaction intermediate (II) is common to the two already mentioned synthesis and can conventionally be obtained by reacting a 1,3-diamino-propyl derivative of general formula (V)

$$NH_2—CH_2—X—CH_2—NH_2 \quad (V),$$

wherein X is as previously described, with methyl or ethyl chloroacetate in a preferably alcoholic solvent and subsequently protecting the hydroxy groups with suitable protecting groups.

Preferred X groups in compounds formula (V) are of —CH(OH)— and —$C(CH_2OH)_2$— residues.

The protection of hydroxy groups in compounds of formula (V) can be also preferably obtained by reacting said compounds with 3,4-dihydro-2H-pyran in an aprotic organic solvent and in the presence of a suitable catalyst, such as for instance pyridinium p-toluenesulfonate (PPTS).

Isophthaldiamides of formula (III) are preferably obtained by reacting 5-acetylamino-2,4,6-triiodoisophthalic acid dichloride with the following hydroxyalkylamines: 2-hydroxy-ethylamine, 1,3-dihydroxy-isopropylamine (serinol), 2,3-dihydroxy-propylamine (isoserinol), 2-amino-1,3,4-butanetriol or N-methylglucamine, following known synthetic processes such as those described in U.S. Pat. No. 4,001,323 and EP 26281.

Condensation reaction of the compounds of formula (II) with the isophthaldiamide reactive derivatives of formula (III) is preferably carried out in an inert organic solvent. Dimethylformamide (DMF) is particularly preferred for most of the compounds of the present invention. The temperature ranges from room to solvent boiling temperature, preferably between 20° and 60° C. Final hydrolysis of hydroxy protecting groups is preferably performed at room temperature in an aqueous solvent acidified at pH values ranging from 1 to 3, preferably 2.

The compounds of the present invention can be used as opacifying agents in non-ionic contrast media for X-ray analysis.

They can be formulated in an appropriate pharmacologically acceptable carrier. Suitable carriers comprise, for instance, those useful for enteral or parenteral administration. Examples of suitable carriers are sterile buffered aqueous solutions containing tromethamine; phosphate ,- citrate, and/or bicarbonate ions, ionically balanced solutions containing physiologically tolerable anions and cations such as $Cl^{(-)}$, $HCO_3^{(-)}$, $Ca^{(2+)}$, $Na^{(+)}$, $K^{(+)}$ and $Mg^{(2+)}$. The solutions of the contrast media of the present invention can also contain a small amount of a physiologically tolerable chelating agent, such as EDTA sodium and calcium salts, in concentrations between 0.05 and 2 mM/l, or even heparin, at a dosage ranging between 5 and 500 units per 100 ml of solution, or in another suitable anticoagulant agent. Hypotonic solutions cf the contrast media of the present invention can be made isotonic by adding a correct amount of Merlis liquid (Am. J. Phy. Vol. 131, 1940 p 67–72 ) . Useful iodine concentrations of said contrast media can range, according to the use, between 140 and 500 mgI/ml at a dosage of 10–300 ml.

The following experimental examples illustrate the basic features of this invention.

EXAMPLE 1

5,5'-[(2-hydroxy-1,3-propanediyl)bis [imino (2-oxo-2,1-ethanediyl) acetylimino]]bis[N,N'-bis(2,3- dihydroxypropyl) -2,4,6-triiodo-1,3-benzenedicarboxyamide].

a) 2-hydroxy-N,N'-1,3-propanediyl-bis (2-chloroacetamide).

Into a three-necked 500 ml flask, equipped with a stirrer, thermometer and a calcium chloride valve, a methyl chloroacetate solution (47 g; 0.433 tool) in 100 ml of $CH_3OH$ is placed and temperature is kept between 0° and 5° C.

A 1,3-diamino-2-hydroxy-propane (18 g; 0.2 tool ) (Rif: Beil. 4H290, E II 739, E IV 1694) solution in 50 ml of $CH_3OH$ is added dropwise into the mixture, under stirring, during three hours while keeping the temperature between 0° and 5° C.

When the operation is completed, temperature is raised to 20°–25° C. and the mixture is kept under stirring overnight. As the reaction is completed, pH is neutral and a white crystalline precipitate is obtained, which is filtered, washed with $CH_3OH$ and dried under vacuum to obtain 37 g of crude 2-hydroxy-N,N'-1,3-propanediyl-bis (2-chloroacetamide). After crystallization from 96% EtOH, 30 g of pure product are obtained.

Yield: 61,7% m.p.: 115° C.

| | Elemental analysis (%) | | | |
|---|---|---|---|---|
| | C | H | Cl | N |
| Calc.: | 34.59 | 4.98 | 29.17 | 11.52 |
| Found: | 34.45 | 4.95 | 28.54 | 11.26 |

IR, $^1H$ and $^{13}C$-NMR spectra are in accordance with the structures.

b) 2-[(tetrahydro-2H-pyran-2-yl)oxy]-N,N'-1,3-propanediyl-bis(2-chloroacetamide).

To a suspension of 2-hydroxy-N,N'-1,3-propanediyl-bis(2-chloroacetamide) (12.16 g; 0.050 mol) and 3,4-dihydro-2H-pyran (6.31 g; 0.075 mol) in 350 ml of $CH_2Cl_2$, 1.25 g of pyridinium p-toluenesulfonate (PPTS) (0.005 mol) are added in portions under stirring at a temperature of 5° C. After 30 minutes, temperature raises up to 20°–25° C. and the stirring is continued during 72 h; the solution is washed with 20% aqueous NaCl (2×100 ml), dried over $Na_2SO_4$ and concentrated to dryness under vacuum. The residue solidifies in n-hexane, and then after filtration, is crystallized from EtOH (115 ml) to obtain 14.1 g of 2-[(tetrahydro-2H-pyran-2-yl)oxy]-N,N'-1,3-propanediyl-bis(2-chloroacetamide).

Yield: 86% m.p.: 100° C.

| | Elemental analysis (%) | | | |
|---|---|---|---|---|
| | C | H | Cl | N |
| Calc.: | 44.05 | 6.16 | 21.67 | 8.56 |
| Found: | 44.16 | 6.20 | 20.70 | 8.53 |

IR, $^1H$ and $^{13}C$-NMR spectra are in accordance with the structures.

c) N,N'-bis(2,3-dihydroxypropyl)-5-acetylamino-2,4,6-triiodo-1,3-benzenedicarboxyamide.

In a three-necked 500 ml flask, 13.6 g (0.15 mol) of 1-amino-2,3-dihydroxy-propane are dissolved in 100 ml of dimethyl acetamide (DMAC). The temperature is decreased to +3°–5° C. Then a solution of 19.1 g (0.03 mol) of 5-acetylamino-2,4,6-triiodo-isophthalic acid dichloride (obtained according to the synthesis scheme described in U.S. Pat. No. 4,001,323 and EP 26281) in 60 ml of DMAC is added dropwise under stirring for 1 h.

The temperature raises between 20° and 25° C., and 3 h later the solvent is evaporated and an oily residue is obtained, which is diluted with water and kept under stirring up to its trans formation into a white solid.

After filtration, the product is suspended in 150 ml of $CH_3OH$ and boiled for 2 h more. After cooling, the crystalline solid is filtered and dried to obtain 14.9 g of N,N'-bis(2,3-dihydroxypropyl)-5-acetyl-amino-2,4,6-triiodo-1,3-benzenedicarboxyamide.

Yield: 66.5% m.p.: 292°–295° C. (dec)

d) 5,5'-[(2-hydroxy-1,3-propanediyl)bis[imino (2-oxo-2,1-ethanediyl)acetylimino]]bis[N,N'-bis(2,3-dihydroxypropyl)-2,4,6-triiodo-1,3-benzenedicarboxyamide].

9.13 g (0.012 mol) of N,N'-bis(2,3-dihydroxypropyl)-5-acetylamino-2,4,6-triiodo-1,3-benzenedicarboxyamide, obtained according to procedure c), are suspended in 130 ml of DMF at 40° C., under stirring and inert atmosphere ($N_2$). 12.2 ml (0.012 mol) of 1M $CH_3ONa$ in $CH_3OH$ are slowly added dropwise to the suspension. As soon as a clear solution is obtained the alcoholic solvent is removed under reduced pressure, therefore 2 g (0.006 mol) of 2-[(tetrahydro-2H-pyran-2-yl)oxy]-N,N'-1,3-propanediyl-bis(2-chloroacetamide) are added according to procedure b). The mixture is reacted at 40° C. under stirring for 17 h, then the solvent is evaporated under vacuum and the oily residue is diluted many times with $CH_2Cl_2$ and dried to remove totally the residual solvent. A solid product is obtained which is diluted in 75 ml of $H_2O$. The pH of the solution is adjusted to 2 with 1N HCl and kept constant at room temperature for 20 h until the tetrahydropyranyl protecting group is completely hydrolysed.

Finally, the aqueous solution is percolated in succession on 20 ml of Amberlite$^{(R)}$ IR 120 and on 50 ml of IRA$^{(R)}$ 400. The eluate obtained from ion-exchange resins is concentrated to about 100 ml, treated for 30 rain with Amberlite$^{(R)}$XAD-2 resin and finally concentrated to dryness. The residue (7.18 g) is cromatographed on 50 ml of silica gel 60F. Merck (230–400 mesh).

Eluting mixture: $CH_2Cl_2/CH_3OH$ of 3/1 to 0/1 (v/v). The recovered product (5.46 g) is crystallized twice from $CH_3OH/EtOH$ to obtain 3.95 g of 5,5'-[(2-hydroxy-1,3-propanediyl)bis [imino(2-oxo-2,1-ethanediyl)acetylimino]] bis[N,N'-bis(2,3-dihydroxypropyl)-2,4,6-triiodo-1,3-benzenedicarboxyamide].

Yield: 86%

| | Elemental analysis (%) | | | |
|---|---|---|---|---|
| | C | H | I | N |
| Calc.: | 28.15 | 3.03 | 45.75 | 6.73 |
| Found: | 28.32 | 3.03 | 45.72 | 6.56 |

EXAMPLE 2

5,5'-[(2-hydroxy-1,3-propanediyl)bis [imino (2-oxo-2,1ethanediyl) acetylimino]]bis[N,N'-bis(1,3-dihydroxyisopropyl)-2,4,6-triiodo-1,3-benzenedicarboxyamide].

a) N,N'-bis(1,3-dihydroxypropyl)-5-acetylamino-2,4,6-triiodo-1,3-benzenedicarboxyamide.

Following the procedure described in EXAMPLE 1 c), 4.53 g (0.05 mol) of 1-hydroxymethyl-2-hydroxy-ethylamine are reacted in 40 ml of DMAC with 6.36 g (0.01 mol) of 5-acetylamino-2,4,6-triiodo-isophthalic acid dichloride in 50 ml of DMAC in order to obtain 4.5 g N,N'-his (1,3-dihydroxyisopropyl)-5-acetylamino-2,4,6-triiodo-1,3-benzenedicarboxyamide which is controlled in $^1H$ and $^{13}C$-NMR spectroscopy and used without additional purification.

b) 5,5'-[(2-hydroxy-1,3-propanediyl)bis [imino (2-oxo-2,1-ethanediyl)acetylimino]]bis[N,N'-bis(1,3-dihydroxyisopropyl)-2,4,6-triiodo-1,3-benzenedicarboxyamide].

Following the procedure described in EXAMPLE 1 d), 4.2 g (0.0056 mol) of N,N'-bis(1,3-dihydroxyisopropyl) -5-acetylamino-2,4,6-triiodo-1,3-benzenedicarboxyamide, suspended in 50 ml of DMF, are reacted with 5.6 ml (0.0056 mol) of 1M $CH_3ONa$ in $CH_3OH$. The resulting amide sodium salt is then reacted with 1 g (0.003 mol) of 2-[(tetrahydro-2H-pyran -2-yl)oxy]-N,N'-1,3-propanediyl-bis(2-chloroacetamide) to obtain the desired condensation product that, after hydrolysis of the protecting group and subsequent purification, yields 1.26 g of 5,5'-[(2-hydroxy -1,3-propanediyl)bis [imino(2-oxo-2,1-ethanediyl) acetylimino]]bis [N,N'-bis(1,3-dihydroxyisopropyl) -2,4,6-triiodo-1,3-benzenedicarboxyamide].

Yield: 25.2%

| | Elemental analysis (%) | | | | |
| --- | --- | --- | --- | --- | --- |
| | C | H | I | N | |
| Calc.: | 28.15 | 3.03 | 45.75 | 6.73 | |
| Found: | 28.01 | 3.18 | 45.50 | 6.50 | ($H_2O$:1.75%) |

In a similar way the following compounds were obtained:

5,5'-[(2-hydroxy-1,3-propanediyl)bis [imino(2-oxo -2,1-ethanediyl)acetylimino]]bis[N,N'-bis-(2-hydro -xy-ethyl)-2,4,6-triiodo-1,3-benzenedicarboxyamide].

5,5'-[(2-hydroxy-1,3-propanediyl)bis [imino(2-oxo -2,1-ethanediyl)acetylimino]]bis[N,N'-bis-(1,3,4 -trihydroxy-2-butyl)-2,4,6-triiodo-1,3-benzenedicarboxyamide].

5,5'-[[2,2-bis(hydroxymethyl)-1,3-propanediyl] -bis-[imino(2-oxo-2,1-ethanediyl)acetylimino]]bis -[N, N'-bis(2-hydroxyethyl)-2,4,6-triiodo-1,3 -benzenedicarboxyamide].

5,5'-[[2,2-bis(hydroxymethyl)-1,3-propanediyl]bis -[imino(2-oxo-2,1-ethanediyl)acetyl-imino]]bis [N, N'-bis(1,3-dihydroxyisopropyl)-2,4,6-triiodo-1,3- benzenedicarboxyamide].

5,5'-[[2,2-bis(hydroxymethyl)-1,3-propanediyl]bis -[imino(2-oxo-2,1-ethanediyl)acetyl-imino]]bis[N,N' -bis(2,3-dihydroxypropyl)-2,4,6-triiodo-1,3-benzenedicarboxyamide].

5,5'-[[2,2-bis(hydroxymethyl)-1,3-propanediyl]bis -[imino(2-oxo-2,1-ethanediyl)acetyl-imino]]bis [N,N' -bis(1,3,4-trihydroxy-2-butyl)-2,4,6-triiodo-1,3-benzenedicarboxyamide].

We claim:

1. Symmetrical and asymmetrical 5,5'-[(1,3-propanediyl) bis[imino(2-oxo-2,1-ethanediyl)acetylimino]]bis -(2,4,6-triiodo-1,3-benzenedicarboxyamides) of general formula (I)

wherein:

R,R',$R_1$,$R_1$', which can be the same or different, are H, $C_1$–$C_4$ alkyl, linear for branched $C_1$–$C_4$ mono- or polyhydroxyalkyl, $R_2$,$R_2$' which can be the same or different, are one of the groups of formula —$CH_2CH_2OH$, —$CH_2CH(OH)CH_2OH$, —$CH(CH_2OH)CH(OH)CH_2OH$, —$CH_2(CHOH)_4CH_2OH$ or —$CH(CH_2OH)_2$, X is one of the groups —CH(OH)—, —CH($CH_2OH$)—, —C(OH)($CH_2OH$)— or —C($CH_2OH$)$_2$—, as well as enantiomers, diastereoisomers and/or rotamers thereof.

2. Compounds according to claim 1, where in R, R', $R_1$, $R_1$' are H and X is —CH(OH)—.

3. Compounds according to claim 1, wherein R, R', $R_1$, $R_1$', are H and X is —C($CH_2OH$)$_2$'.

4. Compounds according to claim 1, wherein R, R', $R_1$, $R_1$' are H, $R_2$, $R_2$', $R_3$, $R_3$' are groups of formula —CH($CH_2OH$)$_2$ and/or —$CH_2CH(OH)CH_2OH$, X is —CH(OH)—.

5. A compound according to claim 1, selected from:

5,5'-[(2-hydroxy-1,3-propanediyl)bis[imino(2-oxo -2,1-ethanediyl)acetylimino]]bis[N,N'-bis(2,3 -dihydroxypropyl)-2,4,6-triiodo-1,3-benzenedicarboxyamide].

5,5'-[(2-hydroxy-1,3-propanediyl)bis[imino(2-oxo -2,1-ethanediyl)acetylimino]]bis[N,N'-bis(1,3 -dihydroxyisopropyl)-2,4,6-triiodo-1,3-benzenedicarboxyamide].

5,5'-[(2-hydroxy-1,3-propanediyl)bis[imino(2-oxo -2,1-ethanediyl)acetylimino]]bis[N,N'-bis(2 -hydroxyethyl)-2,4,6-triiodo-1,3-benzenedicarboxyamide].

5,5'-[(2-hydroxy-1,3-propanediyl)bis[imino(2-oxo -2,1-ethanediyl)acetylimino]]bis[N,N'-bis(1,3,4 -trihydroxy-2-butyl)-2,4,6-triiodo-1,3-benzenedicarboxyamide].

5,5'-[[2,2-bis(hydroxymethyl)-1,3-propanediyl] -bis [imino(2-oxo-2,1-ethanediyl)acetylimino]]bis -[N, N'-bis(2-hydroxyethyl)-2,4,6-triiodo-1,3- ben-zenedicarboxyamide].

5,5'-[[2,2-bis(hydroxymethyl)-1,3-propanediyl] -bis [imino(2-oxo-2,1-ethanediyl)acetylimino]]bis -[N, N'-bis(1,3-dihydroxyisopropyl)-2,4,6-triiodo-1,3- ben-zenedicarboxyamide].

5,5'-[[2,2-bis(hydroxymethyl)-1,3-propanediyl]bis -[imino(2-oxo-2,1-ethanediyl)acetylimino]]bis[N,N' -bis(2,3-dihydroxypropyl)-2,4,6-triiodo-1,3-benzenedicarboxyamide].

5,5'-[[2,2-bis(hydroxymethyl)-1,3-propanediyl]bis -[imino(2-oxo-2,1-ethanediyl)acetylimino]]bis[N,N' -bis(1,3,4-trihydroxy-2-butyl)-2,4,6-triiodo-1,3-benzenedicarboxyamide].

6. Non-ionic X-ray contrast media containing as opacifying component at least one iodinated compound according to claim 1.

7. A X-ray contrast medium according to claim 6 containing as opacifying component 5,5'-[(2-hydroxy-1,3-propanediyl)bis[imino(2-oxo-2,1-ethanediyl)acetylimino]] bis] N,N'-bis(2,3-dihydroxypropyl)-2,4,6-triiodo-1,3- benzenedicarboxyamide].

8. A X-ray contrast medium according to claim 6 containing as opacifying component 5,5'-[(2-hydroxy-1,3-propanediyl) bis[imino(2-oxo-2,1-ethanediyl)acetylimino]] bis[ N,N'-bis(1,3-dihydroxyisopropyl)-2,4,6-triiodo-1,3- benzenedicarboxyamide].

* * * * *